United States Patent [19]
Galler

[11] Patent Number: 6,087,332
[45] Date of Patent: Jul. 11, 2000

[54] STREPTOKINASE DERIVATIVES WITH HIGH AFFINITY FOR ACTIVATED PLATELETS AND METHODS OF THEIR PRODUCTION AND USE IN THROMBOLYTIC THERAPY

[76] Inventor: Lawrence Isaac Galler, 19 Treeway Ct., 1C, Towson, Md. 21286

[21] Appl. No.: 08/997,532

[22] Filed: Dec. 23, 1997

[51] Int. Cl.$^7$ .................................................. A61K 38/00
[52] U.S. Cl. ........................... 514/12; 435/216; 435/440; 424/94.64; 514/2; 536/23.2; 536/23.4
[58] Field of Search ..................... 435/216, 440; 424/94.64; 514/2, 12; 536/23.2, 23.4

[56] References Cited

U.S. PATENT DOCUMENTS

| | | | |
|---|---|---|---|
| 4,764,469 | 8/1988 | Ferretti ..................................... | 435/216 |
| 5,149,780 | 9/1992 | Plow et al. . | |
| 5,187,098 | 2/1993 | Malke et al. . | |
| 5,204,445 | 4/1993 | Plow et al. . | |
| 5,242,810 | 9/1993 | Maraganore et al. . | |
| 5,272,162 | 12/1993 | Tjoeng et al. . | |
| 5,318,899 | 6/1994 | Scarborough et al. . | |
| 5,344,783 | 9/1994 | Scarborough et al. . | |
| 5,344,837 | 9/1994 | Tjoeng et al. . | |
| 5,354,738 | 10/1994 | Tjoeng et al. . | |
| 5,384,309 | 1/1995 | Barker et al. . | |
| 5,493,007 | 2/1996 | Burnier et al. . | |
| 5,496,724 | 3/1996 | Scarborough et al. . | |
| 5,602,155 | 2/1997 | Ruminski . | |
| 5,609,869 | 3/1997 | Quertermous et al. . | |
| 5,612,311 | 3/1997 | Pierschbacher et al. . | |
| 5,635,477 | 6/1997 | Degrado et al. . | |
| 5,643,872 | 7/1997 | Ali et al. . | |
| 5,648,330 | 7/1997 | Pierschbacher ........................... | 514/11 |

OTHER PUBLICATIONS

Beasley et al, "Protein Design: The Choice of de Novo Sequences", *J. Biol. Chem.*, 272(4):2031–2034 (1997).

Branden et al, eds. *Introduction to Protein Structure*, Garland Publishing, Inc., New York (1991) pp. 241, 247–254.

Damashum et al, "Streptokinase is a flexible multi–domain protein", *Eur. Biophys. J.*, 20:355–361 (1992).

Lin et al, "Mutation of Lysines in a Plasminogen Binding Region of Streptokinase Identifies Residues Important for Generating a Functional Activator Complex", *Biochemistry*, 35:16879–16885 (1996).

Martin, Lawrence, "*We Can't Kill Your Mother*" and Other Stories of Intensive Care, "Crisis and Lysis", (1997).

Medved et al, "Domain structure, stability and interactions in streptokinase", *Eur. J. Biochem*, 239:333–339 (1996).

Nihalani et al, "Streptokinase Contains Two Independent Plasminogen–Binding Sites", *Biochem. & Biophys. Research Communications*, 217(3):1245–1254 (1995).

Oxender et al, eds., *Protein Engineering*, Alan R. Liss, Inc., New York (1987), pp. xv–xvi, 5, 15, 33, 35, 221.

Young et al, "Interaction of Streptokinase and Plasminogen", *J. Biol. Chem.*, 270(49):29601–29606 (1995).

"Thrombolytic Therapy in Thrombosis", *NIH Consensus Statement*, 3(1):1–6 (1980).

Diatide Company Press Release, "Diatide, Inc. Receives Research Grant from the National Institute of Health", Apr. 12, 1997.

"Fibrolase–GPIIb/IIIa–avid peptide chimera: A platelet targeted thrombolytic agent", *Thrombosis & Stasis Supplement*, OC–781, p. 193 (Jun. 9, 1997).

"t–PA and the Thrombolytic Debate", *Medical Sciences Bulletin*, published by Pharmaceutical Information Associates, Ltd.

"Why Aren't Thrombolytics Used More Often?", *Medical Sciences Bulletin*, published by Pharmaceutical Information Associates, Ltd.

"Pulmonary embolism: Targeting an elusive enemy", *Nursing 96* (Apr. 1996).

*Primary Examiner*—Karen Cochrane Carlson
*Attorney, Agent, or Firm*—Browdy and Neimark

[57] ABSTRACT

Streptokinase derivatives having platelet glycoprotein binding domains adjacent to the termini of the streptokinase sequence. These derivatives produce higher local concentrations of plasmin in vivo as compared to unmodified streptokinase. Certain of the derivatives have high affinity for the GPIIB/IIIA receptor and low affinity for the fibronectin and vitronectin receptors. Others have substantially equivalent affinity for all three receptors. The derivatives are useful in treating thromboembolic disorders. The streptokinase derivatives can be made by recombinant techniques or by chemical synthesis or conjugation.

28 Claims, No Drawings

STREPTOKINASE DERIVATIVES WITH HIGH AFFINITY FOR ACTIVATED PLATELETS AND METHODS OF THEIR PRODUCTION AND USE IN THROMBOLYTIC THERAPY

FIELD OF THE INVENTION

The present invention relates to streptokinase derivatives with platelet glycoprotein binding domains adjacent to the termini of the streptokinase sequence. These compounds produce higher local concentrations of plasmin in vivo as compared to unmodified streptokinase. Certain of the derivatives have high affinity for the GPIIB/IIIA receptor and low affinity for the fibronectin and vitronectin receptors. Others have substantially equivalent affinity for all three receptors. The present invention also relates to methods of using the compounds of the invention for the treatment of thromboembolic disorders.

BACKGROUND OF THE INVENTION

The principal pharmacological use of streptokinase is in the promotion of clot lysis. Streptokinase (SK), a 47-kDa protein overproduced by β-hemolytic Streptococci Groups A, B, and C forms a 1:1 stoichiometric complex with human plasminogen (Pg). While no proteolytic activity has been associated with streptokinase, in vivo formation of the heterogeneous SK-Pg dimer (activator complex) results in conformational changes to the plasminogen moiety leading to exposure of an enzymatic active center. This center is capable of proteolytic cleavage of uncomplexed zymogenic plasminogen into the fibrinolytic enzyme Plasmin (Pn). Plasmin cleaves the insoluble protein polymer fibrin, a major structural component of the thrombus, into small, soluble degradation products. Sufficient degradation of fibrin elements results in clot dissolution and lysis.

Thrombus formation is characterized by rapid conformational changes to blood platelets and activation of various plasma proproteins. In response to a range of triggering stimuli, zymogenic prothrombin is catalyzed to thrombin. In turn, thrombin acts upon the soluble structural protein fibrinogen, cleaving the N-terminal A and B polypeptides from the α and β chains to form fibrin monomer. Cleavage results in redistribution of charge density and exposure of two polymerization sites, enabling growth of the monomer into an insoluble, three dimensional polymeric network. Concurrently, thrombin, in the presence of ADP and the divalent cation $Ca^{2+}$, acts to induce significant physiological changes to a "resting" or inactive blood platelet, including thromboxane $A_2$ synthesis and the release of ADP from intraplatelet storage granules. Such activated platelets are capable of binding fibrinogen, polymerizing fibrin monomer, and fibrin polymer at the platelet GPIIB/IIIA glycoprotein. This binding results in the rapid formation of a three dimensional hemostatic plug, which serves to rapidly induce loss of circulatory system integrity.

Thrombus formation in the absence of vessel trauma or rupture is pathogenic, and is a causative factor in ischemic heart disease (myocardial infarction, unstable angina), ischemic stroke, deep vein thrombosis (DVT), pulmonary embolism (PE), and related conditions.

Appearance of atherosclerotic plaques within the coronary arteries is the precursor to ischemic heart disease (IHD). Disruption of the endothelial layer of coronary arteries by lipid-filled foam cells is followed by microlesions in or rupture of the endothelial wall. Either Event results in exposure of platelet activation compounds within the intima, including tissue factor plasminogen activator and collagen. Platelet aggregation results in thrombus formation at the site of plaque rupture. Mural thrombi extend within this ruptured plaque into the vessel volume. Small, non-occlusive mural thrombi may oscillate in response to pressure variations within the vessel, resulting in transient stenosis of the affected channel. Such time-variant blockage is characteristic of unstable angina. Larger, occlusive mural thrombi may completely block the affected vessel, resulting in myocardial infraction and/or patient death.

Causative factors for ischemic stroke include cardiogenic emboli, atherosclerotic emboli, and penetrating artery disease. Cardiogenic emboli are generated within the left atrium and ventricle as a result of valve disease or cardiomyopathy. Migration of the embolus through the aorta into the carotids results in stenosis of a cerebral vessel. As in IHD, atherosclerotic plaques within the carotids or cerebral vasculature serve as loci for the formation of mural thrombi. Vascular disease can result in hypercoagulative states, resulting in thrombus formation. Consequences of ischemic stroke include loss of function of the affected region and death.

Pulmonary embolism results from the migration of the embolus from a formation site within the deep veins of the extremities into the pulmonary vasculature. In the event of an acute blockage, consequences include rapid death by heart failure. Pulmonary hypertension frequently results.

Formation of emboli within the deep veins of the lower extremities is characterized as deep vein thrombosis. Causative factors include atherosclerotic plaques and blood stasis. Certain surgical procedures also correlate strongly with postoperative venous clot formation. These include hip or knee replacement, elective neurosurgery, and acute spinal cord injury repair.

Thrombolytic Therapy

Therapeutic lysis of pathogenic thrombi is achieved through administration of thrombolytic agents. Benefits of thrombolytic therapy include rapid lysis of the thromboembolic disorder and restoration of normal circulatory function. Complications include internal and external bleeding due to lysis of physiologic clots, and stroke resulting cerebral hemorrhage. Currently available treatments are presented in tabular format below. Each of these agents promotes the activation of the proenzyme plasminogen into the fibrin degrading protease plasmin.

| Characteristic | Streptokinase | Anistreplase | Urokinase | tPA |
| --- | --- | --- | --- | --- |
| Molecular weight (kDa) | 47 | 131 | 31–55 | 70 |
| Plasma Clearance time (min) | 15–25 | 50–90 | 15–20 | 4–8 |
| Fibrin Specificity | Minimal | Minimal | Moderate | Moderate |
| Plasminogen Binding | Indirect | Indirect | Direct | Direct |
| Potential Allergic Reaction | Yes | Yes | No | No |
| Approximate Cost | $200–300 | $2000 | $2750 | $2200 |
| Typical Dose | 1.5 million units | 30 units | 2 million units | 15 mg |
| Administration | 1 hr IV infusion | 5 min IV infusion | 1 million unit IV bolus, then 1 million units IV over 1 hr | 15 mg bolus, then 0.75 mg/kg over 30 min |

The efficacy of thrombolytic therapy in the treatment of myocardial infarction was demonstrated by the APSAC intervention mortality study. Patients presenting within six hours of onset of acute myocardial infarction (AMI)

received intravenous APSAC or a placebo. The APSAC group demonstrated a 47% reduction in mortality over the control. Studies assessing the relative merits of competing thrombolytics in the treatment of acute myocardial infarction include GISSI-2, ISIS-3, GUSTO. GISSI-2 compared tissue plasminogen activator (tPA) vs. streptokinase administered within six hours of acute myocardial infarction. Overall mortality was similar (tPA 9.0%, SK, 8.6%). Reinfarction was significantly lower with tPA (tPA 1.9%, SK 2.3%). Incidence of hemorrhagic stroke was similar (tPA 0.3%, streptokinase 0.25%), while major bleeds were higher with SK (tPA 0.5%, streptokinase 1.0%).

A subsequent meta-study encompassing GISSI-2 and 8401 additional patients resulted in similar results; overall mortality: tPA 8.9%, SK 8.5%; hemorrhagic stroke: tPA 0.6% SK 0.4%; major bleeds: tPA 0.7%, SK 0.8%. I,3IS-3 compared SK vs. tPA vs. anistreplase in patients presenting within 24 hr of AMI. Overall mortality rates were comparable (SK 10.6%, tPA 10.3%, APSAC 10.5%). Major bleeds were somewhat more frequent with APSAC and SK (SK 0.9%, tPA 0.8%, APSAC 0.1%). Significantly fewer instances of hemorrhagic stroke were observed with SK (SK 0.2%, tPA 0.7%, APSAC 0.5%). Reinfarction results were similar to GISSI-2 (SK 3.5%, tPA 2.9%, ASPAC 3.6%). tPA was thus noted to provide more rapid coronary artery patency than SK or APSAC. GUSTO mortality results were again, comparable, with the advantage to tPA (SK 7.3%, tPA 6.3%).

Establishment of patency within the occluded artery varies with time and thrombolytic administered. An accelerated tPA regimen resulted in highest patency rates at 90 minutes (accelerated tPA 83%, tPA 70%, APSAC 70%, UK 60%, SK 54%). However, patency rates converge rapidly over the next 90 minutes and are substantially equivalent at 24 hours.

Successful application of thrombolytics in ischemic stroke has not been realized. Primary factors mitigating against $$X_1X_2X_3X_4\text{-Gly-Asp-}X_5X_6X_7X_8 \quad \text{(SEQ ID NO:1)}$$

wherein $X_1$ is zero or at least one amino acid. If $X_1$ is one amino acid, it is either the positively charged residue Lys or Arg;

$X_2$ is Cys or an amino acid analog capable of forming a bridge;

$X_3$ is zero or at least one amino acid;

$X_4$ is the positively charged residue Lys or Arg;

$X_5$ is selected from among Ala, Val, Phe, Pro, Met, Ile, Leu, or Trp;

$X_6$ is absent or is Pro or Gly;

$X_7$ is Cys or an amino acid analog capable of forming a bridge;

$X_8$ is zero or at least one amino acid. If $X_8$ is one amino acid, it is either the positively charged residue Lys or Arg;

Specific examples of polypeptides according to the present invention include the following:

The recombinant streptokinase derivatives of the present invention display increased specificity for activated platelets, and thus achieve the above cited design goals.

The streptokinase derivatives of the present invention are produced using molecular cloning techniques in which competent E. coli are transformed with pThioHis expression plasmids. These plasmids carry ligated DNA inserts coding for fusion proteins within the open reading frame of thioredoxin:

A recombinant DNA molecule comprising the following elements in the 5' to 3' direction, wherein said elements are operably linked:

- a DNA sequence encoding the first part of a fusion protein, said DNA sequence encoding streptokinase. In a preferred embodiment, the streptokinase is derived from *Streptococcus equisimilis* strain H46A;
- a polylinker or restriction sequence;
- a DNA sequence encoding the peptide $X_1X_2X_3X_4$-Gly-Asp-$X_5X_6X_7X_8$ wherein
- $X_1$ is absent or at least one of the group consisting of Lys and Arg;
- $X_2$ is Cys or an amino acid analog capable of forming a bridge;
- $X_3$ is absent or at least one amino acid;
- $X_4$ is the positively charged residue Lys or Arg;
- $X_5$ is selected from the group consisting of Ala, Val, Phe, Pro, Met, Ile, Leu, and Trp;
- $X_6$ is absent or Pro or Gly;
- $X_7$ is Cys or an amino acid analog capable of forming a bridge.
- $X_8$ is zero or at least one amino acid.

Of particular importance are recombinant DNA molecules wherein the peptide is one of the following:

| | |
|---|---|
| Arg-Cys-Gly-Arg-Gly-Asp-Trp-Pro-Cys-Arg | (SEQ ID NO:2) |
| Lys-Cys-Gly-Arg-Gly-Asp-Trp-Pro-Cys-Arg | (SEQ ID NO:3) |
| Lys-Cys-Gly-Lys-Gly-Asp-Trp-Pro-Cys-Arg | (SEQ ID NO:4) |
| Arg-Cys-Gly-Lys-Asp-Gly-Trp-Pro-Cys-Arg | (SEQ ID NO:5) |

Additionally, the invention comprises a recombinant DNA molecule comprising the following elements in the 5' to 3' direction, said elements being operably linked:

- a DNA sequence encoding a peptide $X_1X_2$ $X_3X_4$-Gly-Asp-$X_5X_6X_7X_8$ (SEQ ID NO:1) according to claim 1;
- a polylinker or restriction sequence;
- a DNA sequence encoding the first part of a fusion protein, said DNA sequence encoding streptokinase;
- a polylinker or restriction sequence; and
- a DNA sequence encoding the peptide $X_1X_2X_3X_4$-Gly-Asp-$X_5X_6X_7X_8$ (SEQ ID NO:1).

The advantages of the streptokinase derivatives of the present invention are as follows:

1. Preferential ligation of streptokinase derivatives to the acute thrombus resulting in:
   a. high local concentrations of streptokinase derivatives;
   b. reduced concentrations of streptokinase derivatives in global circulatory system resulting in reduced risk of hemorrhaging or uncontrolled bleeding;

to an inducible, expressed carrier protein but upstream of its termination sequence. Successful expression is followed by proteolytic cleavage of the carrier protein. The preferred embodiment is the pThioHis vector, which has proven to be useful for large-scale expression of soluble fusions.

pThioHis contains an altered tray gene coding for a mutant thioredoxin with high affinity for divalent cations. This allows for rapid purification of expressed fusions via metal chelate affinity chromatography (MCAC). Specifically Glu-31, Glu-63 in wild-type thioredoxin have been mutated to His-31, His-63. Tertiary interaction with the His-7 site results in a histidine patch, with the aforementioned affinity for chelate species. 3' to trxA is an enterokinase recognition and cleavage site (Asp-Asp-Asp-Asp-Lys) (SEQ ID NO:11), which provides for cleavage of the desired protein form the thioredoxin carrier following chromatographic purification. 3' to the enterokinase site is a polylinker, or multiple cloning site (MCS) to facilitate oriented ligation of the desired insert. Expression of the fusion is controlled by the inducible trc(trp-lac) promoter. During amplification, expression is halted by the lacI$^q$ repressor, located on the plasmid. Addition of isopropyl-βD-thiogalactopyranoside (IPTG) results in disassociation of the lacI$^q$ repressor product from the lacO operator, allowing transcription.

SUMMARY OF THE INVENTION

It is an object of the present invention to overcome the aforementioned deficiencies in the prior art.

It is another object of the invention to provide compounds for thrombolytic therapy which have high affinity for activated platelets.

It is another object of the present invention to provide derivatives of streptokinase which have a high affinity for activated platelets.

It is a further object of the present invention to provide a method for producing streptokinase derivatives using molecular cloning techniques.

Streptokinase derivatives have now been made which have a high affinity for activated platelets of an acute thrombus. The specificity only for activated platelets of an acute thrombus, rather than for all platelets, confers increased potency, efficacy, and reduced side effects as compared to conventional thrombolytic compounds.

The recombinant streptokinase hybrids (rSK$_{DV}$) of the present invention contain the primary stricture of streptokinase, SK, and one or two platelet glycoprotein-binding polypeptides operably linked to either the C-terminal or both the C- and the N-termini of the streptokinase domain. The primary structure of the polypeptides is designed in accordance with the general parameters discussed above, with a secondary β-turn engineered by the inclusion of two bridge-forming residues into the polypeptide chain. These polypeptides have the following formulae:

$X_1X_2X_3X_4GDX_5X_6X_7X_8$  (SEQ ID NO:1)

wherein $X_1$ is zero or at least one amino acid. If $X_1$ is one amino acid, it is either the positively charged residue Lys or Arg;

$X_2$ is Cys or an amino acid analog capable of forming a bridge;

$X_3$ is zero or at least one amino acid;

$X_4$ is the positively charged residue Lys or Arg;

$X_5$ is selected from among Ala, Val, Phe, Pro, Met, Ile, Leu, or Trp;

$X_6$ is absent or is Pro or Gly;

$X_7$ is Cys or an amino acid analog capable of forming a bridge;

$X_8$ is zero or at least one amino acid. If $X_8$ is one amino acid, it is either the positively charged residue Lys or Arg;

Specific examples of polypeptides according to the present invention include the following:

Arg-Cys-Gly-Arg-Gly-Asp-Trp-Pro-Cys-Arg  (SEQ ID NO:2)

Lys-Cys-Gly-Arg-Gly-Asp-Trp-Pro-Cys-Arg  (SEQ ID NO:3)

Lys-Cys-Gly-Lys-Gly-Asp-Trp-Pro-Cys-Arg  (SEQ ID NO:4)

Arg-Cys-Gly-Lys-Asp-Gly-Trp-Pro-Cys-Arg  (SEQ ID NO:5)

The recombinant streptokinase derivatives of the present invention display increased specificity for activated platelets, and thus achieve the above cited design goals.

The streptokinase derivatives of the present invention are produced using molecular cloning techniques in which competent *E. coli* are transformed with pThioHis expression plasmids. These plasmids carry ligated DNA inserts coding for fusion proteins within the open reading frame of thioredoxin:

A recombinant DNA molecule comprising the following elements in the 5' to 3' direction, wherein said elements are operably linked:

a DNA sequence encoding the first part of a fusion protein, said DNA sequence encoding streptokinase. In a preferred embodiment, the streptokinase is derived from *Streptococcus equisimilis* strain H46A;

a polylinker or restriction sequence;

a DNA sequence encoding the peptide $X_1X_2X_3$ $X_4$Gly-Asp$X_5X_6X_7X_8$ (SEQ ID NO:1) wherein $X_1$ is absent or at least one of the group consisting of Lys and Arg;

$X_2$ is Cys or an amino acid analog capable of forming a bridge;

$X_3$ is absent or at least one amino acid;

$X_4$ is the positively charged residue Lys or Arg;

$X_5$ is selected from the group consisting of Ala, Val, Phe, Pro, Met, Ile, Leu, and Trp;

$X_6$ is absent or Pro or Gly;

$X_7$ is Cys or an amino acid analog capable of forming a bridge.

$X_8$ is zero or at least one amino acid.

Of particular importance are recombinant DNA molecules wherein the peptide is one of the following:

Arg-Cys-Gly-Arg-Gly-Asp-Trp-Pro-Cys-Arg  (SEQ ID NO:2)

Lys-Cys-Gly-Arg-Gly-Asp-Trp-Pro-Cys-Arg  (SEQ ID NO:3)

Lys-Cys-Gly-Lys-Gly-Asp-Trp-Pro-Cys-Arg  (SEQ ID NO:4)

Arg-Cys-Gly-Lys-Asp-Gly-Trp-Pro-Cys-Arg  (SEQ ID NO:5)

Additionally, the invention comprises a recombinant DNA molecule comprising the following elements; in the 5' to 3' direction, said elements being operably linked:

a DNA sequence encoding a peptide $X_1X_2$ $X_3$ $X_4$Gly-Asp$X_5X_6X_7X_8$ (SEQ ID NO:1) according to claim 1;

a polylinker or restriction sequence;

a DNA sequence encoding the first part of a fusion protein, said DNA sequence encoding streptokinase;

a polylinker or restriction sequence; and a DNA sequence encoding the peptide $X_1X_2$ $X_3$ $X_4GDX_5X_6X_7X_8$ (SEQ ID NO:1).

The advantages of the streptokinase derivatives of the present invention are as follows:

1. Preferential ligation of streptokinase derivatives to the acute thrombus resulting in:
   a. high local concentrations of streptokinase derivatives;
   b. reduced concentrations of streptokinase derivatives in global circulatory system resulting in reduced risk of hemorrhaging or uncontrolled bleeding;

c. reduced dosage required to achieve therapeutic concentrations local to the thrombus.
2. Relatively high plasminogen to plasmin conversion activity at the surface of the acute throb)us, resulting in:
   a. high local concentrations of plasmin;
   b. increased fibrinolytic activity at the locus of the thrombus;
   c. reduced thrombolysis time, resulting in faster restoration of normal circulatory function.
3. Competitive inhibition between platelet aggregation processes and streptokinase derivatives ligation resulting in:
   a. diminished rates of clot aggregation;
   b. reduced thrombolysis time;
   c. reduction or elimination of need for separate anticoagulant therapy.
4. Significant enhancement in potency of low-cost streptokinase, resulting in creation of potentially lowest cost per dosage thrombolytic agent in existence. This reduction in cost can be expected to make thrombolytic therapy more attractive to clinicians, especially within a managed care environment.
5. The combination of low therapeutic dosages, diminished risk of uncontrolled bleeding and low cost may allow the use of streptokinase derivatives of the present invention by emergency or outpatient practitioners as a new modality for immediate therapeutic treatment of time-critical thromboembolic disorders, including ischemic stroke, myocardial infarction, or massive pulmonary embolism.

DETAILED DESCRIPTION OF THE INVENTION

The streptokinase derivatives of the present invention thus comprise streptokinase to which is conjugated a platelet aggregation inhibitor at the C-terminal, or C- and N-terminal of the streptokinase. In a preferred embodiment of the invention, the platelet aggregation inhibitor is specific to GPIIB/IIIA. In other embodiments, the platelet aggregation inhibitor has substantially equivalent affinity for the GPIIB/IIIA receptor, for the fibronectin receptor, and for the vitronectin receptor.

The streptokinase derivatives of the present invention, which are fusion proteins, thus contain at least one platelet glycoprotein binding domain as well as the functional component of the streptokinase molecule. After selection and cloning of the transformed E. coli, the expression product is isolated from the medium.

In a typical compound, the N-terminus domain of the expressed protein is thioredoxin, the central region is streptokinase, and the C-terminus domain is a platelet binding peptide containing two bridge forming residues. Following protein isolation, the N-terminal thioredoxin is cleaved with enterokinase and removed from solution via affinity chromatography. The protein is then exposed to an oxidizing medium to promote formation of a disulfide bridge within the platelet binding domain. The resultant purified, folded protein can then be administered in a therapeutic dosage in a physiologically acceptable carrier for the treatment of thromboembolic disorders.

Administering a therapeutic dosage of a streptokinase derivative of the present invention results in sufficient concentrations local to the thrombus to provide fibrinolysis, while highly dilute concentrations of the derivative are distributed in the circulatory system. Furthermore, fibrinolytic activity is proportional to the size and activity of the thrombus. In the absence of a major thrombus or embolism, the streptokinase derivative will not produce significant fibrinolytic activity or degradation of coagulation factors. Thus, if a patient is mistakenly diagnosed with a thrombus and the streptokinase derivative of the present invention is administered, there is no danger of bleeding from administration of a thrombolytic compound that is unneeded. If there is no thrombus or embolism, the streptokinase derivative will not affect bleeding because it is specific for a thrombus or embolism, and is not attracted to platelets which are not activated.

The streptokinase derivatives of the present invention can safely be administered to patients who are mistakenly diagnosed with a thrombus or embolism because these streptokinase derivatives have a high affinity for GPIIB/IIIA receptors. This IIB/IIIA affinity can be determined, as for example, by a liposome attachment assay, as described in Example3 IV and VI or in a platelet aggregation assay as described in Example V of Piersbacher et al., U.S. Pat. No. 5,648,330, the entire contents of which are hereby incorporated by reference. Peptides characterized by a high affinity for GP IIB/IIIA will have an $IC_{50}$ as measured under the assay conditions provided in Examples IV and VI of Piersbacher et al., ibid of less than about 10 $\mu$m, preferably less than about 1 $\mu$m, and more preferably about 0.1 $\mu$m. Alternatively, affinity for GP IIB/IIIA as characterized in Example V of Piersbacher et al. will have an $IC_{50}$ of less than about 10 $\mu$m, preferably lees than about 1 $\mu$m, and more preferably about 0.1 $\mu$m. Using these assays, under the conditions described, one skilled in the art can readily screen various peptides in order to determine their inhibitory concentrations, and therefore their binding affinities, and to select those having high affinity for GP IIB/IIIA, without undue experimentation.

The following examples describe the synthesis of the streptokinase derivatives of the present Invention. These examples are intended for illustration only, and are not intended to limit the invention to these specific examples.

EXAMPLE I

Preparation of DNA Insert
1.1 Genomic DNA is Isolated from S. equisimilis

Streptococcus equisimilis (American Type Culture Collection; #12499) was inoculated in 5 mL of Brain Heart Infusion medium (Difco Laboratories; catalog #1700-37-8) and grown to mid-log phase (12 hours at 37° C.). Bacterial genomic DNA was collected, through phenol extraction and ethanol precipitation. 1.5 mL of cell culture was collected in a microcentrifuge tube, centrifuged for 2 minutes, and the supernatant decanted. The resulting pellet: was resuspended in 567 $\mu$L TE Buffer [10 mM TrisCl, pH 7.5; 1 mM EDTA, pH 8.0] by repeated pipetting. A proteinase solution [30 $\mu$L 10% sodium dodecyl sulfate (SDS); 3 $\mu$L 20 mg/ml Proteinase K] was added to the cell suspension to a final concentration of 100 $\mu$g/ml Proteinase K in 0.5% SDS. The suspension was mixed, then incubated for 1 hr at 37° C. 100 $\mu$L of 5M NaCl was added to preclude formation of cetyl-trimethylammonium bromine (CTAB)-nucleic acid precipitates. Proteins and polysaccharides were precipitated from solution by the addition of 80 $\mu$L CTAB-NaCl [100% CTAB; 0.7M NaCl], followed by mixing and 10 min of incubation at 65° C. An equal volume of 24:1 (v/v) chloroform/isoamyl alcohol was added, mixed, and spun 5 min to extract CTAB-linked precipitates. The supernatant was decanted into a new microcentrifuge tube. An equal volume of 25:24:1 (v/v/v) phenol/chloroform/isoamyl alcohol was added, mixed thoroughly to promote extraction, and spun for 5 min. The supernatant was transferred to a new microcentrifuge tube. Nucleic acids were precipitated by addition of 0.6 vol of isopropanol. The precipitate was pelleted, and the supernatant decanted. The pellet was washed in 70% ethanol and respun. The supernatant was removed and the pellet dried, followed by resuspension in 100 µL TE buffer. 2 µL of RNase (2 mg/ml) were added to obtain a final RNase concentration of 40 µg/ml. The DNA was incubated at 37° C. for 30 minutes. Yield was approximately 5–20 µg DNA/ml cell culture. Excess DNA was stored at +4° C.

1.2 PCR Amplification of the skc Gene

Amplification of skc was via the Polymerase Chain Reaction of Saiki et al. Two oligonucleotide primers were manufactured consisting of skc terminal base-pair complements plus a restriction site to facilitate oriented ligation. 25-mer 5' TT GGT ACC T ATT GCT GGA CCT GAG T 3' (SEQ ID NO:6) (Kpn I site underlined, 48% G-C, $T_m$=69° C., M.W.= 8.126 KDa) and 26-mer 5' GC TCT AGA TTT GTC GTT AGG GTT ATC 3' (SEQ ID NO:7) (Xba I site underlined, 42% G-C, $T_m$=69° C., M.W.=8.264 KDa). Number of nucleotides 5' to type II endonuclease recognition sequence was selected to promote efficient cleavage in accordance with previous experimental results (New England Biolabs; 1997 catalog). The base 3' to the Kpn I sequence maintains the insert within the ORF of the expression vector, resulting in the conservation the Pro-131 codon (CC[wobble]) between the enterokinase recognition site of the vector and N-terminal of the skc expression product.

A 100 µL reaction volume was assembled in a 500 µL thin-walled reaction tube (Perkin-Elmer; part no. N801-0737) consisting of 10 µL 10X PCR buffer (Perkin-Elmer; part no. N808-0006) [500 mM KCl; 100 mM TrisHCl, pH 8.3; 15 mM MgCl$_2$, 0.01% (w/v) gelatin], 200 µM each dNTP, 0.5 µL (2.5 U) AmpliTaq Gold DNA Polymerase (Perkin-Elmer; part no. N808-0242), 500 ng bacterial genomic DNA, 400 ng each primer (0.5 µM each), and sterile, filtered water, pH 20 7.0 to 100 µL. 50 µL of mineral oil (Perkin-Elmer; part no. 0186-2302) was added to control evaporation. The reaction tube was loaded into a Perkin-Elmer Cetus DNA Thermal Cycler 480 thermocycler and subject to a 10 minute preincubation step at 94° C., followed by 30 cycles of 60 sec at 95° C. and 50 seconds of 25 polymerization at 72° C. The final step was a 10 min hold at 72° C. 100 µL of chloroform was added, and the DNA-containing low-density aqueous layer was collected. The amplification products were electrophoretically resolved on a 1.5% agarose gel. The fragment corresponding to the length of the skc gene (1259 bp) was recovered, purified, and aliquoted into 100 ng portions.

The skc amplification product was digested using XbaI (New England BioLabs; catalog no. 145L). A 20 µL reaction volume was prepared by adding to a sterile microcentrifuge tube 100 ng of skc, 2.0 µL 10X Restriction Digest Buffer [50 mM NaCl; 10 mM TrisHCl; 10 mM MgCl$_2$; 1 mM dithiothreitol, pH 7.9; 2 µg bovine serum albumin (BSA)], 0.1 µL (2 U) XbaI, sterile, distilled water to 20 µL final volume. The reaction was incubated for 1 hr at 37° C., followed by irreversible heat inactivation at 65° C. for 20 min. The resulting undesired terminal fragment was separated using gel electrophoresis. The skc fragment was recovered and purified.

1.3 The Platelet Binding Polypeptide is Synthesized and Ligated to skc

Oligonucleotide cassettes coding for 5' to 3': a XbaI restriction site, a platelet glycoprotein binding polypeptide (pbp), and a PstI restriction site were synthesized using automated techniques. A typical cassette sequence was 5' GCTCT AGA TGT AAG GGC GAT TGG CCT TGT CGA TAG CTG CAG AA 3' (SEQ ID NO:8).

The number of nucleotides 5' to type II endonuclease recognition sequence was selected to promote efficient cleavage in accordance with previous experimental results (New England Biolabs). [Ligation of the XbaI-digested 5' end to the XbaI digested 3' end of the skc amplification product resulted in introduction of a de novo serine codon (TCT)].

The pbp was digested with XbaI to obtain compatible cohesive ends with the skc fragment. A 20 µL reaction volume was prepared by adding to a sterile microcentrifuge tube 100 ng of pbp, 2.0 µL 10X Restriction Digest Buffer [50 mM NaCl; 10 mM TrisHCl; 10 mM MgCl$_2$; 1 mM dithiothreitol, pH 7.9; 2 µg bovine serum albumin (BSA)], 0.1 µL (2 U) XbaI, and sterile, distilled water to 20 µL final volume. The reaction was incubated for 1 hr at 37° C., followed by irreversible heat inactivation at 65° C. for 20 min. The resulting undesired terminal fragment was separated using a 20' polyacrylamide gel. The pbp was recovered and purified.

The digested cassette was ligated to the digested skc amplification product. Based on a j:i ratio of 1–3 and an skc size of 1.257 kbp, a desired skc concentration of 15–45 µg/ml per ligation mixture was determined. 200 ng of skc in a 10 µL reaction volume (20 µg/ml) yielded 24.4 nM final skc concentration. A 1:1 skc:pbp molar ratio resulted in 24.4 nM final pbp concentration, or 7 ng of pbp. 200 ng skc and 7 ng pbp were added to a sterile microcentrifuge tube. Sterile, filtered water was added to 7.5 µL and the tube warmed to 45° C. for 5 min, then brought to 0° C. The following components were then added: 1 µL 10X T4 DNA Ligase Buffer [200 mM TrisHCl, pH 7.6; 50 mM MgCl$_2$; 50 mM dithiothreitol; 500 µg/ml BSA], 0.1 U T4 DNA Ligase (New England Biolabs; catalog no. 202S), and 1 µL 5 mM ATP. The reaction was incubated at 16° C. for four hours. T4 Ligase was thermally inactivated by heating to 70° C. for 10 min. The ligation products were resolved via agarose gel electrophoresis, and the desired insert eluted and purified.

The skc-pbp insert was digested with KpnI and PstI to produce correctly oriented cohesive ends for ligation into the expression A vector. A 20 µL reaction volume was prepared by adding to a sterile microcentrifuge tube 100 ng of skc-pbp, 2.0 µL 10X Restriction Digest Buffer [50 mM NaCl; 10 mM TrisHCl; 10 mM MgCl$_2$; 1 mM dithiothreitol, pH 7.9; 100, µg/ml BSA], 0.1 µL (2 U) PstI (New England Biolabs; catalog no. 140S), 0.2 µL (2 U) KpnI (New England Biolabs; catalog no. 142S) and sterile, distilled water to 20 µL final volume. The reaction was incubated for 1 hour at 37° C. The digestion products were resolved via agarose gel electrophoresis, and the desired insert eluted and purified.

EXAMPLE II

Preparation of Plasmid 2.1 The pThioHis A Vector is Prepared

The following examples utilized the His-Patch ThioFusion™ Expression System Version A (Invitrogen; catalog no. K360-01). 20 µg lyophilized pThioHis A plasmids were resuspended in 20 µL sterile water to a final concentration of 1 µg/1 µL, aliquoted into 100 ng portions and stored at −20° C.

A 20 µL reaction volume was prepared by adding to a sterile microcentrifuge tube 100 ng of plasmid, 2.01 µL 10X Restriction Digest Buffer [50 mM NaCl; 10 mM TrisHCl; 10 mM MgCl$_2$; 1 mM dithiothreitol, pH 7.9; 100 µg/ml BSA], 0.1 µL (2 U) PstI (New England Biolabs; catalog no. 140S), 0.2 μL (2 U) KpnI (New England Biolabs; catalog no. 142S) and sterile, distilled water to 20 μL final volume. The reaction was incubated for 1 hour at 37° C. The stuffer fragment was eliminated via gel electrophoresis, and the linearized vector eluted and purified.

2.2 The Insert is Ligated to the pThioHis A Vector

The insert was ligated to the linearized vector. Based on a j:i ratio of 1–3 and a digested vector size of 4.305 kbp, a desired vector concentration of 8–25 μg/ml per ligation mixture was determined. 100 ng of vector in a 10 μL reaction volume (10 μg/ml) yielded 3.55 nM final vector concentration. A 1:3 vector:insert ratio resulted in approximately 10 nM final insert concentration, or 85 ng of insert. 100 ng vector and 85 ng insert were added to a sterile microcentrifuge tube. Sterile, filtered water was added to 7.5 μL and the tube warmed to 45° C. for 5 min, then brought to 0° C. The following components were then added: 1 μL 10X T4 DNA Ligase Buffer [200 mM TrisHCl, pH 7.6; 50 mM $MgCl_2$; 50 mM dithiothreitol; 500 μg/ml BSA], 0.1 U T4 DNA Ligase (New England Biolabs; catalog no. 202S), and 1 μL 5 mM ATP. The reaction was incubated at 16° C. for four hours. T4 Ligase was thermally inactivated by heating to 70° C. for 10 min.

2.3 Chemically Competent Hosts are Prepared

TOP10 E. coli (Invitrogen) [Genotype:F-mcrA Δ(mrr-hsdRMS-mcrBC) φ80 lacZΔM15 ΔlacX74 deoR real araD139 Δ(ara-leu)7697 galU galKrpsL endA1 nupG] were made chemically competent. Any suitable recA1, endA1 host is usable. Such hosts include JM109 (ATC #53323). TOP10 calls were streaked on an LB plate [1% tryptone; 0.5% yeast extract; 1% NaCl; deionized water to 1 L], the plate inverted, and incubated at 37° C. overnight. 5 mL of SOB Medium [2% tryptone; 0.5% yeast extract; 0.05% NaCl; 2.5 mM KCl; 10 mM $MgCl_2$; deionized water to 1 L] in a sterile culture tube was inoculated with one colony from the LB plate, and grown overnight with shaking (37° C., 200 rpm). 250 mL of fresh SOB medium in a 1 L flask was inoculated with 2.5 ml of the overnight culture and grown in a shaking incubator (37° C., 200 rpm) until $OD_{550}$ reached 0.55–0.65. The culture was equally divided between two +4° C. 250 mL centrifuge bottles and placed on ice for 30 minutes. The bottles were then centrifuged at 2000 g for 10–15 minutes at +4° C. The supernatant was decanted and each pellet resuspended in 10 mL +4° C. FSB transformation solution [10 mM Potassium acetate, pH 7.5; 45 mM $MnCl_2$-$4H_2O$; 10 mM $CaCl_2$-$2H_2O$; 100 mM KCl; 3 mM hexaaminecobalt (III) chloride; 10% glycerol, titrated with 0.1N HCl to final pH 6.4]. The resuspended pellet was divided between two +4° C. 50 mL centrifuge tubes. The tubes were centrifuged at 2000 g for 10–15 min at +4° C. The supernatant was decanted, and each pellet resuspended in 1.3 ml +4° C. FSB transformation solution using a cold (+4° C.) 5 mL pipette. While gently agitating each tube, 65 μL of DMSO was added dropwise. Each tube was incubated on ice for 15 minutes, followed by dropwise addition of an additional 65 μL of DMSO. The suspensions were combined into one tube and incubated on ice for 15 min. 30 1.5 mL microcentrifuge tubes were placed on ice. 110 μL of suspension was pipetted into each tube. The aliquots were quick-frozen in a dry ice/ethanol bath, and stored at −70° C.

2.4 Competent Hosts are Transfected with the Vector 1 aliquot of frozen competent E. coli was thawed on ice. 5 μL of ligation reaction was added and mixed gently. The tube was incubated on ice for 30 min, then transferred to a 42° C. water bath for 90 sec, then placed on ice for 1–2 min. 800 μL of room temperature SOC medium [1L SOB medium; 20 mM glucose] was added to each tube and incubated with shaking (37° C., 225 rpm) for 1 hr.

2.5 Transformants are Cloned and Plasmid DNA Isolated

100 μL of transformation mix was plated onto LB-Ampicillin (100 μg/ml Amp) plates, inverted, and incubated at 37° C. overnight. 10 Amp-resistant colonies were selected. Colonies were transferred to a second LB-Amp (100 μg/ml Amp) plate and incubated at 37° C. until approximately 1 mm in diameter. Colonies were transferred to a master LB-Amp (100 μg/ml Amp) plate which was incubated at 37° C. for several hours, then stored at 4° C. for future recovery. Remaining bacteria from each colony on the second plate was transferred into a microcentrifuge tube loaded with 50 μL EDTA (pH 8.0). 50 μL of alkali solution [0.2N NaOH; 0.5% SDS; 20% sucrose solution] was added, and vortexed for 30 sec. The mixture was incubated for 5 min on ice. Bacterial debris was pelleted by centrifugation at 12,000 g for 3 min at 4° C. 50 μL of supernatant was loaded into a 0.7% agarose gel and subject to electrophoresis. The gel was visualized and analyzed for the presence of vector+insert (5.7 kb) or vector alone (4.4 kb). Colonies determined to have the vector+insert were recovered from the thawed master plate.

High-quality plasmid DNA was isolated from positive clones. Said colonies were loaded into 15 mL loosely capped tubes containing 2 mL LB-Amp medium. The suspensions were incubated overnight at 37° C. with vigorous shaking. 1.5 mL of each overnight culture was transferred into a microcentrifuge tube and spun at 12,000 g for 30 sec at 4° C. The culture medium was aspirated, and the pellet resuspended in 100 mL 0° C. buffer [50 mM glucose; 25 mM TrisCl, pH 8.0; 10 mM EDTA, pH 8.0] and vortexed to disperse the pellet. 200 μL of alkali solution [0.2N NaOH; 1% SDS] were added. Contents of the tube were mixed by repeated inversion and stored on ice. 150 μL of ice cold acid solution [60 mL 5M potassium acetate; 115 mL glacial acetic acid; 28.5 mL $H_2O$] was added and vortexed inverted for 10 sec to disperse solution throughout the bacterial lysate. Tube was stored on ice for 5 min, followed by centrifugation at 12000 g for 5 min at +4° C. The supernatant was transferred to a fresh tube. An equal volume of phenol:chloroform was added and mixed by vortexing. Following centrifugation at 12,000 g for 2 min at +4° C., the supernatant was transferred to a fresh microcentrifuge tube. dsDNA was precipitated with 2 volumes of room temperature ethanol. Solution was mixed by vortexing, and let stand for 2 min at room temperature, followed by centrifugation at 12,000 for 5 min at +4° C. The supernatant was removed by aspiration, and the tube inverted to allow all the fluid to drain away. The pellet was rinse(i with 1 mL of 70% ethanol at +4° C. The ethanol was aspirated, and the pellet allowed to air dry for 10 min. Resuspension followed in 50 μL TE buffer [10 mM TrisCl, pH7.5; 1 mM EDTA, pH 8.0]. 1 μL of RNase (1 mg/mL) was added to obtain a final RNase concentration of 20 μg/mL. Excess plasmid DNA was stored at −20° C.

2.6 Plasmid DNA is Sequenced

For each clone, presence, orientation, and reading frame of the insert was verified through sequencing of the the PCR-amplified region of interest. Two oligonucleotide primers were obtained corresponding to recognition sites on the vector upstream and downstream of the insert [18-mer 5' TTCCTCGACGCTAACCTG 3' (SEQ ID NO:9) (55% G-C, $T_m$=61° C.) and 20-mer 5' TGTAAAACGACGGC-CAGTGC 3' (SEQ ID NO:10) (55% G-C, $T_m$=67° C.)]. A 100 μL reaction volume was assembled in a 500 μL thin-walled reaction tube (Perkin-Elmer; part no. N801-0737) consisting of 10 μL 10X PCR buffer (Perkin-Elmer; part no. N808-0006) [500 mM KCl; 100 mM TrisHCl, pH 8.3; 15 mM MgCl$_2$, 0.01% (w/v) gelatin], 200 μM each dNTP, 0.5 μL (2.5 units) AmpliTaq Gold DNA Polymerase (Perkin-Elmer; part no. N808-C242), 50 ng vector, 300 ng each primer (0.5 μM each), and sterile, filtered water, pH 7.0 to 100 μL. 50 μL of mineral oil (Perkin-Elmer; part no. 0186-2302) was added to control evaporation. The reaction tube was loaded into a Perkin-Elmer Cetus DNA Thermal Cycler 480 thermocycler and subject to a 10 min preincubation step at 94° C., followed by 30 cycles of 60 sec at 95° C. and 50 sec of polymerization at 72° C. The final step was a 10 min hold at 72° C. 100 μL of chloroform was added, and the DNA containing low-density aqueous layer was collected. The amplification products were electrophoretically resolved on a 1.5% agarose gel. The band corresponding to the length of the fragment of interest was recovered, purified, and sequenced by automated methods.

2.7 Selection of Positive Clones

Positive clones were streaked to produce single colonies on LB-Amp plates. A single clone was selected and reconfirmed by sequencing. Said colony was inoculated into a 2 mL LB-Amp culture and incubated overnight at 37° C. 0.85 mL portions were combined with 0.15 mL sterile glycerol, vortexed, and transferred to storage tubes. The tubes were quick frozen in a dry ice/ethanol bath, and stored at −70° C.

EXAMPLE III

Expression of Hybrid Protein 3.1 The Fusion Protein is Expressed

The clone was streaked out on an LB-Amp plate and grown overnight at 37° C. 2 mL of LB-Amp medium was inoculated with a single clone and maintained in a shaking incubator (37° C., 200 rpm) overnight. 50 mL of LB-Amp medium was inoculated with 0.2 mL of the overnight culture. The culture was grown with vigorous shaking at 37° C. to mid-log phase (OD$_{550}$=0.6). Protein expression was initiated by the introduction of Isopropyl-β-D-thiogalactopyranoside (IPTG). IPTG was added to a final concentration of 1 μM [0.5 ml of 100 mM IPTG stock solution per 50 ml culture]. The suspension was returned to the incubator and grown for 3 hours. Cells were harvested by centrifugation at 3000 g for 10 minutes at +4° C. The supernatant was discarded and the pellet stored at −80° C.

3.2 The Host Cells are Lysed and Fusion Protein Released

Frozen cells were thawed in a 37° C. water bath and resuspended in 10 mL binding buffer [20 ml sodium phosphate; 500 mM NaCl, pH 7.8]. The suspension was transferred to a 50 mL conical tube, placed on ice, and ultrasonically lysed with a suitable micro-tip equipped hand-held sonicator. The lysate was subject to four successive freeze/thaw cycles. Each cycle consisted of immersion in a dry ice/ethanol bath followed by immersion in a 37° C. water bath. The lysate was treated with RNase and DNase to a final concentration of 5 μL/mL each, and incubated on ice for 15 min. Insoluble debris was pelleted at 3000 g for 15 min at +4° C. The lysate was filtered through an 0.8 μm syringe filter and placed on ice.

3.3 The Fusion Protein is Purified via Metal Chelate Affinity Chromatography (MCAC)

A 10 mL ProBond column (Invitrogen; catalog no. R801-01) [20% slurry of immobilized Ni$^{2+}$ resin; 20% ethanol] was equilibrated in accordance with manufacturer's instructions. The resin was twice resuspended in 5 mL cell lysate and gently agitated for 10 min. The resin was allowed to settle, and the supernatant aspirated. The resin was washed twice by suspension in 4 mL of binding buffer [20 mM sodium phosphate; 500 mM NaCl, pH 7.8], 2 minutes of gentle agitation, and aspiration of supernatant. The column was repeatedly washed in 4 mL wash buffer, pH 6.0 [20 mM sodium phosphate; 500 mM NaCl, pH 6.0] until the OD$_{280}$ of the supernatant fell below 0.01. The column was washed twice in 4 mL wash buffer, pH 5.5 [20 mM sodium phosphate; 500 mM NaCl, pH 5.5] by resuspension, agitation, and aspiration. The lower cap of the column was removed, and the fusion protein was eluted by a flow-through with 5 mL of elusion buffer [20 mM sodium phosphate; 500 mM NaCl, pH 4.01.

3.4 The Thioredoxin Moiety is Cleaved and rSK$_{DV}$ Recovered

The thioredoxin carrier is removed by cleavage with enterokinase (EKMax; Invitrogen; catalog no. E180-01). 5 mL of the low-pH MCAC eluent was dialyzed against 1X EKMax reaction buffer [50 mM TrisHCl, pH 8.0; 1 mM $CaCl_2$; 0.1% Tween-20] to restore neutral pH. The following 30 μL reaction volume was assembled: 20 μg fusion protein, 3 μL 10X EKMax reaction buffer [50 mM TrisHCl, pH 8.0; 1 mM $CaCl_2$; 0.1% Tween-20], 1U EKMax, deionized water to 30 μL. Volume was mixed and incubated at 37° C. overnight. Digestion products were resolved via SDS-PAGE, and the $rSK_{DV}$ recovered. Exposure to an oxidizing environment such as oxygenated water was determined to be sufficient to promote disulfide bridge formation within the platelet binding domain.

The streptokinase derivatives of the present invention include functional derivatives of these peptides. By "functional derivative" is meant a fragment, variant, analog or chemical derivatives of the subject streptokinase derivatives, which terms are defined below. A functional derivative retains at least a portion of the amino acid sequence of the streptokinase derivative of interest, which permits its utility in accordance with the present invention, namely specificity to GP IIB/IIIA. As noted above, this specificity can readily be quantified by determining the $IC_{50}$ according to Piersbacher et al., U.S. Pat. No. 5,648,330.

A "fragment" of the streptokinase derivatives of the present invention refers to any subset of the molecule, that is, a shorter peptide. Fragments of interest, of course, are those which have high specificity to GPIIB/IIIA.

A "variant" of the streptokinase derivatives of the present invention refers to a molecule which is substantially similar to either the entire peptide or a fragment thereof. Variant peptides may be conveniently prepared by direct chemical synthesis of the variant peptide, using methods well known in the art.

Alternatively, amino acid sequence variants of the streptokinase derivatives of the present invention can be prepared by mutations in the DNAs which encode the synthesized streptokinase derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (Cf. European Patent Publication No. EP 75,444).

At the genetic level, these variants ordinarily are prepared by site-directed mutageneis (as exemplified by Adelman et al., *DNA* 2:183 (1983) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of the streptokinase derivatives of the present invention refers to a non-natural molecule which is substantially similar to either the entire molecule or to an active fragment thereof.

A "chemical derivative" of a streptokinase derivative according to the present invention contain3 additional chemical moieties not normally part of the streptokinase derivative amino acid sequence. Covalent modifications of the amino acid sequence are included within the scope of this invention. Such modifications may be introduced into the streptokinase derivatives by reacting targeted amino acid residues off the peptide with an organic derivatizing agent that is capable of reacting with selected side chains or terminal residues.

The types of substitutions which may be made in the streptokinase derivatives of the present invention may be based on analysis of the frequencies of amino acid changes between a homologous protein of different species. Based upon such analysis, conservative substitutions may be defined herein as exchanges within one of the following five groups:

I. Small, aliphatic, nonpolar or slightly polar residues:
  Ala, Ser, Thr, Pro, Gly II. Polar, negatively charged residues and their amides:
  Asp, Asn, Glu, Gln III. Polar, positively charged residues:
  His, Arg, Lys IV. Large, aliphatic nonpolar residues:
  Met, Leu, Ile, Val, Cys V. Large aromatic residues:
  Phe, Try, Trp Within the foregoing groups, the following substitution are considered to be "highly conservative":

Asp/Glu

His/Arg/Lys

Phe/Tyr/Trp

Met/Leu/Ile/Val

Semi-conservative substitutions are defined to be exchanges between two of groups (I)–(IV) above which are limited to supergroup (A), comprising (I), (II), and (III) above, or to supergroup (B), comprising (IV) and (V) above. Substitutions are not limited to the genetically encoded or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with he groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

While the present invention provides recombinant methods for making the streptokinase derivatives, these derivatives may also be made by conventional protein synthesis methods which are well known to those skilled in the art.

Pharmaceutical compositions for administration according to the present invention can comprise at least one streptokinase derivative according to the present invention in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art of treating thromboembolic disorders, including ischemic stroke, myocardial infarction, or pulmonary embolism.

For example, administration can b)e by parenteral, such as subcutaneous, intravenous, intramuscular, intraperitoneal, transdermal, or buccal routes. The dosage administered depends upon the age, health and weight of the recipient, type of previous or concurrent treatment, if any, frequency of the treatment, and the nature of the effect desired.

Compositions within the scope of this invention include all composition comprising at least one streptokinase derivative according to the present invention in an amount effective to achieve its intended purpose. While individual needs vary, determination of optimal ranges of effective amounts of each component is within the skill of the art. Typical dosages comprise about 0.1 to about 100 mg/kg body weight.

It should also be understood that to be useful, the treatment provided need not be absolute, provided that it is sufficient to carry clinical value. An agent which provides treatment to a lesser degree than do competitive agents may still be of value if the other agents are ineffective for a particular individual, if it can be used in combination with other agents to enhance the overall level of protection, or if it is safer than competitive agents.

It is understood that the suitable dose of a composition according to the present invention will depend upon the age, sex, health and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This typically involves adjustment of a standard dose, e.g., reduction of the dose if the patient has a low body weight.

Prior to use in humans, a drug is first evaluated for safety and efficacy in laboratory animals. In human clinical trials, one begins with a dose expected to be safe in humans, based on the preclinical data for the drug in question, and on customary doses for analogous drugs, if any. If this dose is effective, the dosage may be decreased to determine the minimum effective dose, if desired. If this dose is ineffective, it will be cautiously increased, with the patients monitored for signs of side effects. See, e.g., Berkow et al., eds., *The Merck Manual*, 15th edition, Merck and Co., Rahway, N.J., 1987; Goodman et al., eds, Goodman and Gilman's *The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD., Williams and Wilkins, Baltimore, Md. (1987); Ebadi, *Pharmacology*, Little, Brown and Co., Boston (1985), which references and references cited therein are entirely incorporated herein by reference.

The total dose required for each treatment may be administered in multiple doses or in a single dose. The compositions may be administered alone or in conjunction with other therapeutics directed to the disease or directed to other symptoms thereof.

In addition to the compounds of the invention, a pharmaceutical composition may contain suitable pharmaceutically acceptable carriers, such as excipients, carriers and/or auxiliaries which facilitate processing of the active compounds into preparations which can be used pharmaceutically.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the futures exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Sambrook, J., Fritsch, E. F., and T. Maniatis, Molecular Cloning: A Laboratory Manual, Cold Spring Harbor Laboratory Press, 1989.

Ausubel, F. M. et al., Current Protocols in Molecular Biology, John Wiley and Sons, New York, 1937.

Brockway, W. J. and F. J. Castellino, A characterization of native streptokinase and altered streptokinase isolated from a human plasminogen activator complex, *Biochem*, 13(10): 2063–2070, 1974.

Taylor, F. B. and P. C. Comp., Biochemistry of streptokinase, In *Fibrinolytics and antifibrinolytics*, F. Markwardt, editor, Springer-Verlag, New York, 137–149, 1978.

Klocking, H. P., Pharmacology of streptokinase, In *Fibrinolytics and antifibrinolytics*, F. Markwardt, editor, Springer-Verlag, New York, 151–177, 1978.

Horst, M., and J. J. Feretti, Strsptokinase: cloning, expression, and excretion by *Escherichia coli, Proc. Nat. Acad. Sci.* USA, 81:3557–3561, 1985.

Horst, M., B. Roe, and J. J. Feretti, Nucleotide sequence of the streptokinase gene from *streptococcus equisimilus* H46A, *Gene*, 34:357–362, 1985.

Friedrich, W., M. Siegel, and H. Malke, Nucleotide sequence of the streptokinase gene from a *streptococcus pyogenes* type 1 strain, *Nucleic Acids Research*, 17(3):1262, 1989.

Friedrich, W., M. Siegel, and H. Malke, Nucleotide sequence of the streptokinase gene from a group-G streptococcus, *Nucleic Acids Research*, 17(3):1262, 1989.

Estrada, M. P., L. Hernandez, A. Perez, P. Rodriguez, R. Serrano, R. Rubiera, A. Pedraza, G. Padron, W. Antuch, J. de la Fuente, and L. Herrera, High level expression of streptokinase in *Escherichia coli, Bio/Tech*, 10:1138–1142, 1992.

Damaschun, G., H. Damaschun, K. Gast, D. Gerlach, R. Misselwitz, H. Welfe, and D. Zirwer, Streptokinase is a flexible multi-domain protein, *Eur Biophys J.*, 20:335–361, 1992.

Teuten, A. J., R. W. Broadhurst, R. A. Smith, and C. M. Dobson, Characterization of structural and folding properties of streptokinase by n.m.r. spectroscopy, *Biochem J.* 290:313–319, 1993.

Medved, L. V., D. A. Dolovjov, and K. C. Ingham, Domain, structure, stability, and interactions in streptokinase, *Eur J. Biochem*, 239:333–339, 1996.

Levine, W. G., Basic principles of clinical pharmacology relevant to cardiology, In *Cardiovascular Pharmacotherapeutics*, W. H. Frishman, and E. H. Sonnenblick, editors, McGraw-Hill, New York, 3–9, 1997.

Rodriguez, P., P. Fuentes, M. Barro, J. G. Alvarez, E. Munuz, D. Collen, and H. R. Lunen, Structural domains of streptokinase involved in the interaction with plasminogen, *Eur J. Biochem*, 229:83–90, 1995.

Young, K., G. Shi, Y. Chang, B. Chang, L. Chang, M. Lai, W. Chuang, and H. Wu, Interaction of streptokinase and plasminogen studied with truncated streptokinase peptides, *J. Bio Chem*, 270(49):29601–29606, 1995.

Nihalani, D. M. and G. Sahni, Streptokinase contains two independent plasminogen-binding sites, *Biochem and Biophys Res Comm.*, 217(3):1245–1254, 1995.

Lin, L. F., S. Oeun, A. Houng, and G. L. Reed, Mutation of lysines in a plasminogen binding region of streptokinase identifies residues important for generating a functional activator complex, *Biochem*, 35:16879–16885, 1996.

Serrano, R. L., P. Rodriguez, S. V. Pizzo, and M. Gonzalez-Gronow, ATP-regulated activity of the plasmin-streptokinase complex: a novel mechanism involving phosphorylation of streptokinase, Biochem J., 313:171–177, 1996.

Gogstad, G. O., F. Brosstad, M. Krutnes, I. Hagen, and N. O. Solum, Fibrinogenbinding properties of the human platelet glycoprotein IIb-IIIa complex: A study using cross-radioimmunoelectrophoresis, Blood, 60(3):663–671, 1982.

Bennet, J. S., The platelet-fibrinogen interaction, In Platelet Membrane Glycoproteins, J. N. George, A. T. Nurden, and D. R. Phillips, editors, Plenum Publishing, New York, 193–214, 1985.

Coller, B. S., Activation affects access to the platelet receptor for adhesive glycoproteins, J. Cell Bio, 103:451–456, 1986.

Shattil, S. J., Expression, regulation and detection of fibrinogen receptors on activated human platelets, In Platelet Membrane Receptors: Molecular Biology, Immunology, Biochemistry, and Pathology, G. A. Jamieson, editor, Alan R. Liss New York, 345–380, 1988.

Charo, I. F., L. Nannizzi, D. R. Phillips, M. A. Hsu, and R. M. Scarborough, Inhibition of fibrinogen binding to GPIIb-IIIa by a GP IIIa peptide, J. Biol Chem, 266(3): 1415–1421, 1991.

Blackmore, C. C., C. W. Francis, R. G. Bryant, B. Brenner, and V. J. Marder, Magnetic resonance imaging of blood and clots in vitro, Inv Rad 25(12):1316–1324, 1990.

Lewis, M. L., D. S. Nachtwey, and K. L. Damron, A miniaturized fibrinolytic assay for plasminogen activators, Thrombosis Research, 64:223–234, 1991.

Pierschbacher, M. D., and E. Ruoslahti, Cell attachment activity of fibronectin can be duplicated by small synthetic fragments of the molecule, Nature, 309:30–33, 1984.

Murayama, M., Decompression inducible platelet aggregation (DIPA) is inhibited by ARG-GLY-ASP, In Platelet Membrane Receptors: Molecular Biology, Immunology, Biochemistry, and Pathology, G. A. Jamieson, editor, Alan R. Liss, New York, 203–209, 1988.

Yasuda, T., H. K. Gold, R. C. Leinbach, H. Yaoita, J. T. Fallon, L. Guerrero, M. A. Napier, S. Bunting, and D. Collen, Kistrin, A polypeptide platelet GPIIb/IIIa receptor antagonist, enhances and sustains coronary arterial thrombolysis with recombinant tissue-type plasminogen activator in a canine preparation, Circulation, 83(3):1038–1047, 1991.

Adler, M., R. A. Lazarus, M.S. Dennis, and G. Wagner, Solution structure of kistrin, a potent platelet aggregation inhibitor and GPIIb-IIIa antagonist, Science, 253:445–448, 1991.

Scarborough, R. M., M. A. Naughton, W. Teng, J. W. Rose, D. R. Phillips, L. Nannizzi, A. Arfsten, A. M. Campbell, and I. F. Charo, Design of potent and specific integrin antagonists: peptide antagonists with high specificity for glycoprotein IIb-IIIa, J Biol Chem, 268(2):1066–1073, 1993.

Lender, A., W. Yao, P. A. Sprengeler, R. A. Spanevello, G. T. F\Purst, R. Hirschmann, and A. B. Smith III, Design and synthesis of sulfur-free cyclic hexapeptides which contain the RGD sequence and bind to fibrinogen GPIIb/IIIa receptor, Int J Pept Prot Res, 42:509–517, 1993.

Scaloni, A., E. Di Martino, N. Miraglia, A. Pelagalli, R. Della Morte, N. Staiano, and P. Pucci, Amino acid sequence and molecular modeling of glycoprotein IIb-IIIa and fibronectin receptor iso-antagonists from Trimeresurus elegans venom, Biochem J, 319:775–782, 1996.

Suehiro, K., J. W. Smith, and E. F. Plow, The ligand recognition specificity of $\beta_3$ integrins, J Bio Chem, 271(17): 10365–10371, 1995.

Scarborough, R. M., J. W. Rose, M. A. Hsu, D. R. Phillips, V. A. Fried, A. M. Campbell, L. Nannizzi, and I. F. Charo, Barbourin: A GPIIb-IIIa specific integrin antagonist from the venom of Sistrurus M. Barbouri, J Bio Chem, 266(15): 9359–9362, 1991.

Gruppo Italiano per lo Studio Della Sopravvivenza Nell'Infarto Miocardico, GISSI-2: A factorial randomized trial of alteplase versus streptokinase and heparin versus no heparin among 12,490 patients with acute myocardial infarction, Lancet, 336:65–71, 1990.

International Study Group, In-hospital mortality and clinical course of 20,891 patients with suspected acute myocardial infarction randomized between alteplase and streptokinase with or without heparin, Lancet, 336:71–75, 1990.

Third International Study of Infarct Survival Collaborative Group, ISIS-3:a randomized comparison of streptokinase vs. tissue plasminogen activator vs. anistreplase and of aspirin plus heparin vs. aspirin alone among 41,299 cases of suspected acute myocardial infarction, Lancet, 339:753–770, 1992.

Dobkin, J. and J. Reichel, Drug treatment in pulmonary embolism, In Cardiovascular Pharmacotherapeutics, W. H. Frishman, and E. H. Sonnenblick, editors, McGraw-Hill, New York, 1165–1171, 1997.

Coffman, J. D., Drug treatment of peripheral vascular disease, In Cardiovascular Pharmacotherapeutics, W. H. Frishman, and E. H. Sonnenblick, editors, McGraw-Hill, New York, 1185–1193, 1997.

Forman, R., and W. H. Frishman, Thrombolytic agents, In Cardiovascular Pharmacotherapeutics, W. H. Frishman, and E. H. Sonnenblick, editors, McGraw-Hill, New York, 381–398, 1997.

Weinberger, J., Drug therapy of neurovascular disease, In Cardiovascular Pharmacotherapeutics, W.:4. Frishman, and E. H. Sonnenblick, editors, McGraw-Hill, New Yore, 1195–1209, 1997.

Freshman, W. H., et al., Antiplatelet and other antithrombotic drugs, In Cardiovascular Pharmacotherapeutics, W. H. Frishman, and E. H. Sonnenblick, editors, McGraw-Hill, New York, 323–379, 1997.

Thrombolysis in Myocardial Infarction Study Group, The thrombolysis in myocardial infarction (TIMI) trial phase I findings, N Engl J Med, 312(14):932–936, 1985.

Myocardial Infarction Study Group, A randomized trial of immediate versus delayed elective angioplasty after intravenous tissue plasminogen activator in acute myocardial infarction, N Engl J Med, 317(10):582–588, 1987.

AIMS Trial Study Group, Effect of intravenous APSAC on mortality after acute myocardial infarction: preliminary report of a placebo-controlled clinical trail, Lance-, 339:753–770, 1988.

Clemetson, K. J., Glycoproteins of the platelet plasma membrane, In Platelet Membrane Glycoproteins, J. N. George, A. T. Nurden, and D. R. Phillips, editors, Plenum Publishing, New York, 51–85, 1985.

Frachet, P., G. Uzan, D. Thevenon, E. Denarier, M. H. Ornadini, and G. Marguerie, GPIIb and GPIIIa amino acid sequences deduced from human megakaryocyte cDNAs, Mol Biol Rep, 14(1):27–33, 1990.

Petersen, T. E., M. R. Martzen, A. Ichinose, and E. W. Davie, Characterization of the gene for human plasminogen, a key proenzyme in the fibrinolytic system, J Biol Chem 265(11):6104–6111, 1990.

Soetinko R., and L. Lenert, Physicians preferences may bias treatment choice for deep venous thrombosis, Unpublished article, Thrombolytic Therapy in Thrombosis, NIH Consens Statement Online Apr. 10–12, 1980, 3(1):1–6, 1997.

Sanger, G., S. Nicklen, and A. R. coulson, DNA sequencing with chain-terminating inhibitors, Proc Natl Acad Sci USA, 74:5463–5467, 1977.

What is claimed is:

1. A recombinant DNA molecule comprising the following elements in the 5' to 3' direction, wherein said elements are operably linked:

a DNA sequence encoding the first part of a fusion protein, said DNA sequence encoding streptokinase;

a polylinker or restriction sequence;

a DNA sequence encoding the peptide $X_1X_2X_3X_4$Gly-Asp$X_5X_6X_7X_8$ (SEQ ID NO:1) wherein $X_1$ is absent or at least one of the group consisting of the positively charged residues Lys and Arg;

$X_2$ is Cys or an amino acid analog capable of forming a bridge;

$X_3$ is absent or at least one amino acid;

$X_4$ is the positively charged Lys or Arg;

$X_5$ is selected from the group consisting of Ala, Val, Phe, Pro, Met, Ile, Leu, and Trp;

$X_6$ is absent or Pro or Gly;

$X_7$ is Cys or an amino acid analog capable of forming a bridge;

$X_8$ is sent or at least one of the group consisting of the positively charged residues Lys or Arg.

2. A recombinant DNA molecule according to claim 1 wherein said streptokinase is derived from β-hemolytic Streptococcus bacteria of Groups A, B, or a.

3. A recombinant DNA molecule according to claim 2 wherein said streptokinase is derived from *Streptococcus equisimilis*.

4. A recombinant DNA molecule according to claim 3 wherein said streptokinase is derived from *Streptococcus equisimilis* strain ATCC 12499.

5. A recombinant DNA molecule wherein according to claim 1 wherein the peptide is selected from the group consisting of:

| | |
|---|---|
| Arg-Cys-Gly-Arg-Gly-Asp-Trp-Pro-Cys-Arg | (SEQ ID NO:2) |
| Lys-Cys-Gly-Arg-Gly-Asp-Trp-Pro-Cys-Arg | (SEQ ID NO:3) |
| Lys-Cys-Gly-Lys-Gly-Asp-Trp-Pro-Cys-Arg | (SEQ ID NO:4) |
| Arg-Cys-Gly-Lys-Asp-Gly-Trp-Pro-Cys-Arg | (SEQ ID NO:5). |

6. A recombinant DNA molecule comprising the following elements in the 5' to 3' direction, wherein said elements are operably linked:

a DNA sequence encoding a streptokinase derived from β-hemolytic streptococci bacteria of groups A, B, or C;

a polylinker or restriction sequence;

a DNA sequence encoding a polypeptide sequence of less than 5 kDa mass which possesses high affinity to at least one of GPIIB/IIIA, vitronectin or fibronectin.

7. A recombinant DNA molecule comprising the following elements in the 5' to 3' direction, wherein said elements are operably linked:

a DNA sequence encoding a polypeptide sequence of less than 5 kDa mass which possesses high affinity to any, some or all of the following platelet membrane receptors, GPIIB/IIIA, vitronectin, or fibronectin;

a polylinker or restriction sequence;

a DNA sequence encoding streptokinase is derived from β-hemolytic Streptococci bacteria of Groups A, B, or C;

a polylinker or restriction sequence;

a DNA sequence encoding a polypeptide sequence of less than 5 kDa mass which possesses high affinity to any, some or all of the following platelet membrane receptors: GPIIB/IIIA, vitronectin, or fibronectin.

8. A fusion protein encoded by the recombinant DNA molecule according to claim 1.

9. A fusion protein encoded by the recombinant DNA molecule according to claim 2.

10. A fusion protein encoded by the recombinant DNA molecule according to claim 3.

11. A fusion protein encoded by the recombinant DNA molecule according to claim 4.

12. A fusion protein encoded by the recombinant DNA molecule according to claim 5.

13. A fusion protein encoded by the recombinant DNA molecule according to claim 6.

14. A fusion protein encoded by the recombinant DNA molecule according to claim 7.

15. A method for treating thromboembolic disorders comprising administering to a patient suffering from a thromboembolic disorder an effective amount of a fusion protein according to claim 8.

16. A method for treating thromboembolic disorders comprising administering to a patient suffering from a thromboembolic disorder an effective amount of a fusion protein according to claim 9.

17. A method for treating thromboembolic disorders comprising administering to a patient suffering from a thromboembolic disorder an effective amount of a fusion protein according to claim 10.

18. A method for treating thromboembolic disorders comprising administering to a patient suffering from a thromboembolic disorder an effective amount of a fusion protein according to claim 11.

19. A method for treating thromboembolic disorders comprising administering to a patient suffering from a thromboembolic disorder an effective amount of a fusion protein according to claim 12.

20. Method for treating thromboembolic disorders comprising administering to a patient suffering from a thromboembolic disorder an effective amount of a fusion protein according to claim 13.

21. A method for treating thromboembolic disorders comprising administering to a patient suffering from a thromboembolic disorder an effective amount of a fusion protein according to claim 14.

22. Composition for treating thromboembolic disorders comprising an effective amount of a fusion protein according to claim 8 in a pharmaceutically acceptable carrier.

23. Composition for treating thromboembolic disorders comprising an effective amount of a fusion protein according to claim 9 in a pharmaceutically acceptable carrier.

24. A composition for treating thromboembolic disorders comprising an effective amount of a fusion protein according to claim 10 in a pharmaceutically acceptable carrier.

25. A composition for treating thromboembolic disorders comprising an effective amount of a fusion protein according to claim 11 in a pharmaceutically acceptable carrier.

26. A composition for treating thromboembolic disorders comprising an effective amount of a fusion protein according to claim 12 in a pharmaceutically acceptable carrier.

27. A composition for treating thromboembolic disorders comprising an effective amount of a fusion protein according to claim 13 in a pharmaceutically acceptable carrier.

28. A composition for treating thromboembolic disorders comprising an effective amount of a fusion protein according to claim 14 in a pharmaceutically acceptable carrier.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (ix) FEATURE:
      (D) OTHER INFORMATION:/note= Xaa in position 1 is optional; if Xaa
         in position 1 is present, it is either the positively
         charged residue Lys or Arg. Xaa in position 2 is Cys or
         an amino acid analog capable of forming a bridge. Xaa in
         position 3 is optional. Xaa in position 4 is the
         positively charged residue Lys or Arg. Xaa in position
         7 is selected from among Ala, Val, Phe, Pro, Met, Ile,
         Leu, or Trp. Xaa in position 8 is absent or is Pro or
         Gly. Xaa in position 9 is Cys or an amino acid analog
         capable of forming a bridge. Xaa in position 10 is
         optional; if Xaa in position 10 is present, it is
         either the positively charged residue Lys or Arg.

(xi) SEQUENCE DESCRIPTION: SEQ ID NO: 1:

```
Xaa Xaa Xaa Xaa Gly Asp Xaa Xaa Xaa Xaa
1               5                   10
```

(2) INFORMATION FOR SEQ ID NO: 2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

```
Arg Cys Gly Arg Gly Asp Trp Pro Cys Arg
1               5                   10
```

(2) INFORMATION FOR SEQ ID NO: 3:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 3:

```
Lys Cys Gly Arg Gly Asp Trp Pro Cys Arg
1               5                   10
```

(2) INFORMATION FOR SEQ ID NO: 4:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 4:

Lys Cys Gly Lys Gly Asp Trp Pro Cys Arg
1               5                   10

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Arg Cys Gly Lys Asp Gly Trp Pro Cys Arg
1               5                   10

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

TTGGTACCTA TTGCTGGACC TGAGT                              25

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:7:

GCTCTAGATT TGTCGTTAGG GTTATC                             26

(2) INFORMATION FOR SEQ ID NO: 8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:8:

GCTCTAGATG TAAGGGCGAT TGGCCTTGTC GATAGCTGCA GAA           43

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

TTCCTCGACG CTAACCTG                                      18

(2) INFORMATION FOR SEQ ID NO: 10:

(i) SEQUENCE CHARACTERISTICS:
        (A) LENGTH: 20 base pairs

-continued

```
        (B) TYPE: nucleic acid
        (C) STRANDEDNESS: single
        (D) TOPOLOGY: linear (xi) SEQUENCE DESCRIPTION: SEQ ID NO:10:

TGTAAAACGA CGGCCAGTGC                                              20

(2) INFORMATION FOR SEQ ID NO: 11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Asp Asp Asp Asp Lys
1               5
```